United States Patent

Temperilli et al.

Patent Number: 5,079,364
Date of Patent: Jan. 7, 1992

[54] T-ALKYL ERGOLINE DERIVATIVES

[75] Inventors: Aldemio Temperilli, Milan; Enzo Brambilla, Comense; Mauro Gobbini, Sesto Calende; Maria A. Cervini, Cardano Al Camp, all of Italy

[73] Assignee: Farmitalia Carlo Erba, Milan, Italy

[21] Appl. No.: 328,518

[22] Filed: Mar. 24, 1989

Related U.S. Application Data

[62] Division of Ser. No. 65,597, Jun. 23, 1987, Pat. No. 4,843,073.

Foreign Application Priority Data

Jun. 25, 1986 [GB] United Kingdom ............... 8615471

[51] Int. Cl.$^5$ .......................................... C07D 457/09
[52] U.S. Cl. .................................................... 546/68
[58] Field of Search ................... 546/67, 68; 514/288

[56] References Cited

U.S. PATENT DOCUMENTS

| Re. 30,218 | 2/1980 | Bach et al. | 546/67 |
| 3,232,942 | 2/1966 | Hofmann et al. | 546/67 |
| 3,959,288 | 5/1976 | Bach et al. | 546/67 |
| 4,197,299 | 4/1980 | Ferrari et al. | 546/67 |

FOREIGN PATENT DOCUMENTS

| 0171988 | 2/1986 | European Pat. Off. |
| 3403067 | 8/1985 | Fed. Rep. of Germany | 546/67 |

OTHER PUBLICATIONS

Morrison and Boyd, Organic Chemistry, [Boston: Allyn and Bacon, 1980] p. 82.

Primary Examiner—Mukund J. Shah
Assistant Examiner—E. C. Ward
Attorney, Agent, or Firm—Oblon, Spivak, McClelland, Maier & Neustadt

[57] ABSTRACT t-alkyl eroline derivatives of formula I are produced

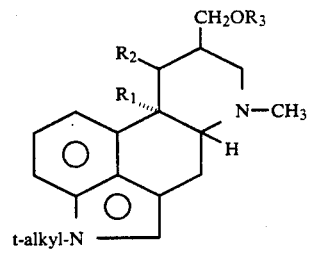

wherein ($R_1$=H, $OCH_3$ and $R_2$H) or ($R_1$+$R_2$=a ring bond and $R_3$=H, optionally substituted nicotinynoyl or 1-oxo-2-cyclopenten-3-yl); and their pharmaceutically acceptable salts.

A process for the preparation of these derivatives from lysergol and a t-alkyl alcohol is also described, as are pharmaceutical compositions containing them.

1 Claim, No Drawings

T-ALKYL ERGOLINE DERIVATIVES

This is a division of application Ser. No. 07/065,597, filed June 23, 1987, now U.S. Pat. No. 4,843,073.

BACKGROUND OF THE INVENTION

1. Field of the Invention

The invention relates to ergoline derivatives, to processes for their preparation and to pharmaceutical compositions containing ergoline derivatives.

2. Discussion of the Background

The 1-alkylation of ergolines may be performed by reacting non-alkylated ergolines with alkyl halides in liquid ammonia in the presence of a strong base such as potassium amide (see Troxler F., Hofmann A., Helv. Chim. Acta, 40 2160 (1957)). The efficiency of this alkylation reaction is good for primary alkyl halides, but much reduced for secondary alkyl halides. Tertiary alkyl halides do not react at all but instead yield the related olefins by elimination.

The prior art has not disclosed a suitable methodology for the addition of a tertiary alkyl group to the 1 position of the ergoline molecule.

SUMMARY OF THE INVENTION

One object of this invention is to provide processes for the preparation of 1-tertiaryalkyl ergoline derivatives, for example, 1-t-butyl ergoline derivatives.

Another object of this invention is to provide 1-tertiaryalkyl ergoline derivatives, for example, 1-t-butyl ergoline derivatives, which are useful as therapeutic agents.

Another object of this invention is to provide pharmaceutical compositions containing such ergoline derivatives.

These and other objects as will hereinafter become more clear from the following disclosure have been attained by preparing 1-(tertiaryalkyl)-ergoline derivatives, e.g. 1-t-butyl ergoline, by using a tertiary alcohol, e.g., t-butanol in trifluoroacetic anhydride, under conditions that one would have expected to lead to electrophilic bonding to position 2 of the ergoline ring or in the aromatic ring. This results in the production of an ergoline derivative of the formula

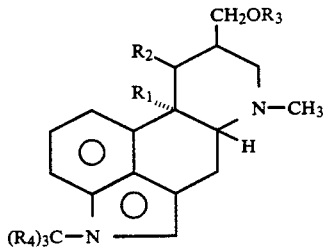

wherein:
R₁ and R₂ taken together represent a ring bond; or
R₁ is a hydrogen atom or a methoxy group and R₂ is a hydrogen atom; or
R₃ is a hydrogen atom, a nicotinoyl group, a substituted nicotinoyl group, or a 1-oxo-2-cyclopenten3-yl group; R₄ is a C₁-C₄ alkyl; or
a pharmaceutically acceptable salt thereof.

DETAILED DESCRIPTION OF THE PREFERRED EMBODIMENTS

Lysergol (II) can be t-alkylated, e.g., t-butylated, at position 1 of the ergoline skeleton by reacting ergoline with tertiary alcohol, e.g., t-butanol, in trifluorcacetic anhydride for a period of from 70 to 90 hours at a temperature between 15°-30° C. and, preferably between 20°-25° C. This reaction may be carried out in the presence or absence of other organic solvents, such as benzene, DMF or dioxane.

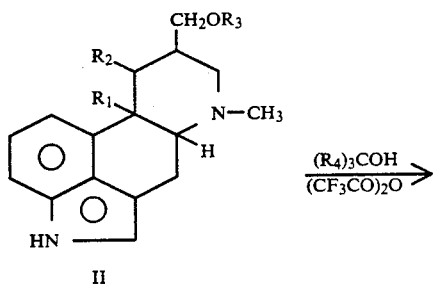

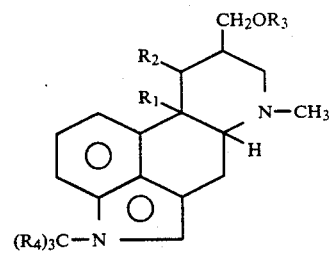

wherein R₁ and R₂ taken together represent a ring bond, and R₃ represents a hydrogen atom and R₄ is independently a C₁-C₄ alkyl, preferably methyl.

The tertiary alkyl lysergol, e.g., t-butyl-lysergol. so obtained may be transformed into a 10-methoxy derivative, according to the process of U.S. Pat. No. 3,647,655 or reduced to the dihydro derivative by reduction with hydrogen in the presence of a noble metal.

The ergoline derivatives of the present invention have the formula I

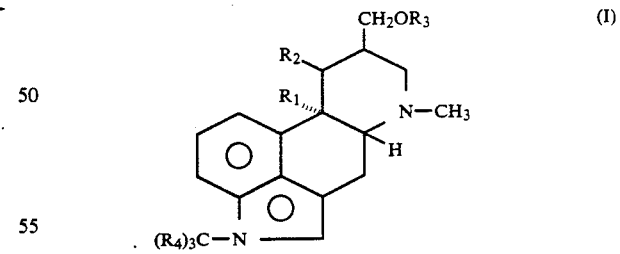

wherein either R₁ represents a hydrogen atom or a methoxy group and R₂ represents a hydrogen atom or R₁ and R₂ taken together form a ring bond, and R₃ represents a hydrogen atom, a nicotinoyl or substituted nicotinoyl group or a 1-oxo-2-cyclopenten-3-yl group; and further provides pharmaceutically acceptable salts of such ergoline derivatives. When R₃ represents a substituted nicotinoyl group, the substituent is preferably an alkyl group having from to 4 carbon atoms, a nitro, cyano, hydroxy, amino or aminomethyl group, or a halogen atom such as a bromine atom. R₄ is independently a $C_{1-4}$ alkyl group, preferably methyl, such that $(R_4)_3C$ is a t-alkyl group.

1-(t-butyl)-10-methoxy-6-methyl-8β-hydroxymethylergoline, 1-(t-butyl)-10-methoxy-6-methyl-8β-(5-bromo-3-pyridine-carboxymethyl)-ergoline and 1-(t-butyl)-10-methoxy- 6-methyl-6β-(1-oxo-2-cyclopenten-3-yloxymethyl)ergoline are some of the preferred compounds of the invention.

The compounds of the invention may be administered in the form of a pharmaceutically acceptable acid addition salt. Such salt forms have the same order of activity as the free base forms.

The tertiary alkyl ergoline derivatives of the invention may be produced by reacting lysergol with an excess quantity of a tertiary alkyl alcohol, e.g., t-butanol, in the presence of a catalytic amount of trifluroacetic anhydride, in the presence or absence of an inert organic solvent, at a temperature between 15° and 30° C. for 70 to 90 hours, preferably at 20–25° C. for 70–90 hours.

The 1-tertiary alkylated lysergol is then either hydrogenated in the presence of a noble metal catalyst, or alkoxylated upon UV irradiation in the presence of an alcohol and sulfuric acid, to form a 1-tertiaryalkylergoline derivative.

The compounds of the general formula I wherein $R_3$ represents a hydrogen atom may be converted into other compounds of the general formula I using normal chemical reactions. For example the esterification of the C-17 hydroxy group is effected by treatment with the anhydride or chloride of an organic acid in the optional presence of a tertiary amine such as pyridine, triethylamine and the like, according to the method described in U.S. Pat. No. 3,228,943 (incorporated by reference herein). The etherification is effected by treatment of the corresponding tosyl esters with 1,3-dicarbonyl compounds in sodium salt form in hexamethylphosphotriamide as solvent as described in U.S. Pat. No. 4,382,940 (incorporated by reference herein). Preferably, this etherification is carried out by reaction with 1,3-cyclopentendione for 2-4 hours at a temperature between 70° C.–100° C.

It has been found that the presence of a t-butyl group in the position 1 of the ergoline skeleton is advantageous in comparison to the presence of a methyl group (U.S. Pat. No. 3,879,554) as shown by electroencephalographic effects (EEG) which show increased and longer-lasting modifications in terms of cortical activation. These modifications suggest the clinical usefulness of these derivatives for the following conditions: diffuse cerebral arteriosclerosis, transient cerebral ischemia and involution syndromes of presenile age, senescence and senility (Buonamici, M., Young, G. A. and Khazan (1982) Neuropharmacology 21 : 825-829, "Effects of Acute $\Delta^9$-THC Administration on EEG and EEG Power Spectra in the Rat").

In this test the compounds were administered at doses of 5-10-20 mg/kg p.o. to groups of 8 rats.

The oral orientative acute toxicity ($LD_{50}$) of the compounds of the formula I was higher than 800 mg/kg.

The compounds are therefore useful in the treatment of cerebral insufficiency and senile dementia, particularly the early stages thereof. For this use the dosage will, of course, vary depending on the compound employed, mode of administration and treatment desired. However, in general, satisfactory results are obtained when administered at a daily dosage of from 0.001 mg to about 50 mg per kg animal body weight, conveniently given in divided doses 2 to 4 times a day or in sustained release form. For the larger mammal, the total daily dosage is in the range of from 1 to about 100, preferably 10 to 90 mg, and dosage forms suitable for oral administration comprise from about 0.2 mg to about 50 mg of the compounds admixed with a solid or liquid pharmaceutically acceptable carrier or diluent, such as starch, lactose, dextrin, magnesium stearate or water.

The present invention accordingly provides a pharmaceutical composition comprising at least one ergoline derivative I as herein defined or a pharmaceutically acceptable salt thereof in admixture with a pharmaceutically acceptable diluent or carrier. Such compositions may be formulated in a conventional manner so as to be, for example, a solution or a tablet. The compounds of the present invention may be used in an analogous manner to standard compounds used for the indications mentioned above.

Other features of the invention will become apparent in the course of the following descriptions of exemplary embodiments which are given for illustration of the invention and are not intended to be limiting thereof.

EXAMPLE 1

1-(t-Butyl)-9,10-didehydro-6-methyl-8β-hydroxymethylergoline

To a mixture of 8 g of lysergol in 150 ml of t-butanol, 200 ml of trifluoroacetic anhydride were added dropwise with vigorous stirring. After the solution had been left at room temperature for 90 hours, it was evaporated. The residue was dissolved in water, made alkaline with ammonium hydroxide and the aqueous layer was extracted with ethyl acetate. After removal of the ethyl acetate, the residue was purified by silica gel column chromatography using 1:1 cyclohexane:ethyl acetate for elution to give 6 g of the title compound melting at 181 to 183° C.

EXAMPLE 2

1-(t-Butyl)-10-methoxy-6-methyl-8β-hydroxymethylergoline

A solution of 6 g of 1-(t-butyl)-9,10-didehydro-6-methyl-8β-hydroxymethyl-ergoline, prepared as described in Example 1, in 500 ml of methanol and 5 ml of sulphuric acid was irradiated at 20° C. in a Pyrex flask with a Hanau PL 321 lamp for about 6 hours, until the absorption at 315 nm completely disappeared. The solution was diluted with iced water, made basic with ammonium hydroxide, evaporated to 100 ml and extracted with ethyl acetate. After evaporation of the solvent the residue was chromatographed in silica gel and on elution with 97:3 dichloromethane:methanol, 5 g of the title compound was isolated, m.p. 172 to 174° C. from acetone.

EXAMPLE 3

1(t-Butyl)-10-methoxy-6-methyl-8β-(5-bromo-3-pyridinecarboxymethyl)-ergoline 2.65 g of 5-bromonicotinoyl chloride were added at 25° C. to a solution of 3 9 of 1-(t-butyl)-10-methoxy-6-methyl-8β-hydroxymethyl-ergoline prepared as described in Example 2, in 35 ml of pyridine. After 4 hours the solution was evaporated in vacuo, the residue was taken up in water containing ammonium hydroxide and extracted with dichloromethane. Evaporation of the solvent left a residue that was purified by chromatography over silica gel using cyclohexane with increasing amounts of acetone (from 0 to 30 percent) as the eluant, to give 4 g of the title compound melting at 75 to 77° C.

EXAMPLE 4

1-(t-Butyl)-10-methoxy-6-methyl-8β-(1-oxo-2-cyclopenten-3-yloxymethyl)-ergoline a) To a solution of 1.8 g of 1-(t-butyl)-10-methoxy-6-methyl-8β-hydroxymethyl-ergoline, prepared as described in Example 2,.in 20 ml of pyridine, 2.8 g of tosyl chloride in 15 ml of pyridine were slowly added. After the addition had been completed, the mixture was stirred for about six hours and was then poured into cold water and extracted with dichloromethane. The organic layer was evaporated off and the residue was chromatographed over 18 g of silica gel using dichloromethane with increasing amounts of methanol (from 0 to 4 percent) as the eluant. 2 g of 1-(t-butyl)-10-methoxy-6-methyl-8β-tosyloxymethyl-ergoline were obtained, melting at about 150 to 152° C.

b) A mixture of 2 g of the compound prepared in the first part of this Example and 0.7 g of 1,3-cyclopentandione sodium salt in 15 ml of hexamethylphosphotriamide was heated at 80° C. for 3 hours. The resulting solution was poured into 200 ml of water and the suspension was extracted with ethyl acetate. After evaporation of the organic solvent the residue was purified by crystallization from diethyl ether to give 1.5 g of the title compound, m.p. 145 to 147° C.

EXAMPLE 5

1-(t-Butyl-6-methyl-8β-hydroxymethyl-ergoline

A solution of 4 g of 1-(t-butyl)-9,10-didehydro-6-methyl-8β-hydroxymethyl-ergoline, prepared as described in Example 1, in 500 ml of methanol was hydrogenated in the presence of 4 g of 10% palladium on carbon catalyst. After removing the catalyst by filtration and the methanol by evaporation, the residue was crystallized from water:methanol to give 3 g of the title compound melting at 162 to 164° C.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. 1-(t-butyl)-10-methoxy-6-methyl-8β-hydroxymethyl-ergoline.

* * * * *